United States Patent [19]
Haslbeck et al.

[11] Patent Number: 5,628,072
[45] Date of Patent: May 13, 1997

[54] EYE GOGGLES WITH LATERALLY ADJUSTABLE EYEPIECES WITHIN GOGGLES FRAME

[75] Inventors: Joseph Haslbeck, West Vancouver; Peter Huopalainen, Surrey, both of Canada

[73] Assignee: Sharp Plastics Manufacturing Ltd., Delta, Canada

[21] Appl. No.: 262,609

[22] Filed: Jun. 20, 1994

[51] Int. Cl.⁶ ........................................... A61F 9/02
[52] U.S. Cl. ..................................... 2/428; 2/441
[58] Field of Search ......................... 2/428, 430, 441, 2/443, 440, 438, 439; 351/43

[56] References Cited

U.S. PATENT DOCUMENTS

| | | | |
|---|---|---|---|
| 2,364,584 | 12/1944 | Malcolm | 2/14 |
| 2,846,684 | 12/1958 | Hill | 2/14 |
| 3,229,303 | 1/1966 | Jonassen | 2/14 |
| 3,610,743 | 10/1971 | Lindholm | 351/107 |
| 3,689,136 | 9/1972 | Atamian | 2/443 X |
| 3,944,345 | 3/1976 | Decorato | 351/43 |
| 4,179,756 | 12/1979 | Lucas | 2/441 X |
| 4,229,837 | 10/1980 | Solari | 2/431 |
| 4,279,028 | 7/1981 | Garofalo | 2/428 |
| 4,367,561 | 1/1983 | Solari | 2/439 |
| 4,468,819 | 9/1984 | Ohno | 2/430 |
| 4,689,838 | 9/1987 | Angermann et al. | 2/441 |
| 4,720,186 | 1/1988 | Douillard | 351/63 |
| 5,093,940 | 3/1992 | Nishiyama | 2/441 |
| 5,111,536 | 5/1992 | Hünnebeck | 2/428 |
| 5,137,341 | 8/1992 | Gendol et al. | 351/43 |

FOREIGN PATENT DOCUMENTS

| | | |
|---|---|---|
| 488094 | 4/1949 | Belgium . |
| 0627850 | 12/1994 | European Pat. Off. . |
| 1200570 | 9/1965 | Germany ............... 351/55 |
| 59-182322 | 12/1984 | Japan . |
| 62-160418 | 7/1987 | Japan . |

OTHER PUBLICATIONS

Leader Industries Inc., New York, "Pivot Hydro Tech" pp. 4, 5, and 25, Published prior to 20 Jun. 1993.

*Primary Examiner*—Peter Nerbun
*Attorney, Agent, or Firm*—Bull, Housser & Tupper

[57] ABSTRACT

A pair of goggles comprises a goggles frame with a pair of eyepiece holders, a nosepiece extending between inner end portions of the eyepiece holders, and a head strap extending between outer end portions of the eyepiece holders. Each eyepiece holder has an opening with an eyepiece unit fitted therein, the eyepiece unit having an overall length less than length of the eyepiece opening to permit relative movement therebetween to vary interocular spacing between the eyepieces to accommodate persons having eyes at different spaces. Guides are provided at outer end portions and intermediate portions of the eyepiece units and eyepiece holders to ensure axial movement of the eyepiece units with respect to the eyepiece holder with negligible rotation therebetween. A locator is provided to limit relative movement between the eyepiece holder and eyepiece unit. The locator can be fitted between adjacent outer end portions of the eyepiece holder and eyepiece unit to prevent movement of the eyepiece unit relative to the eyepiece opening.

23 Claims, 4 Drawing Sheets

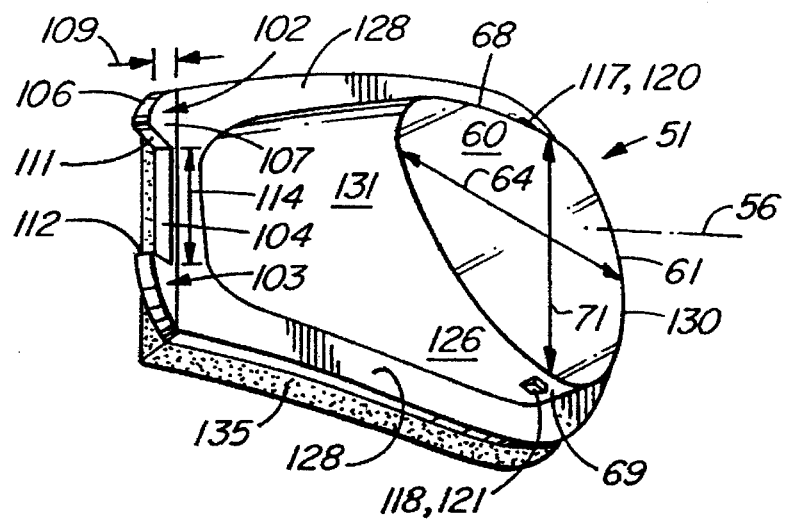
FIG. 4
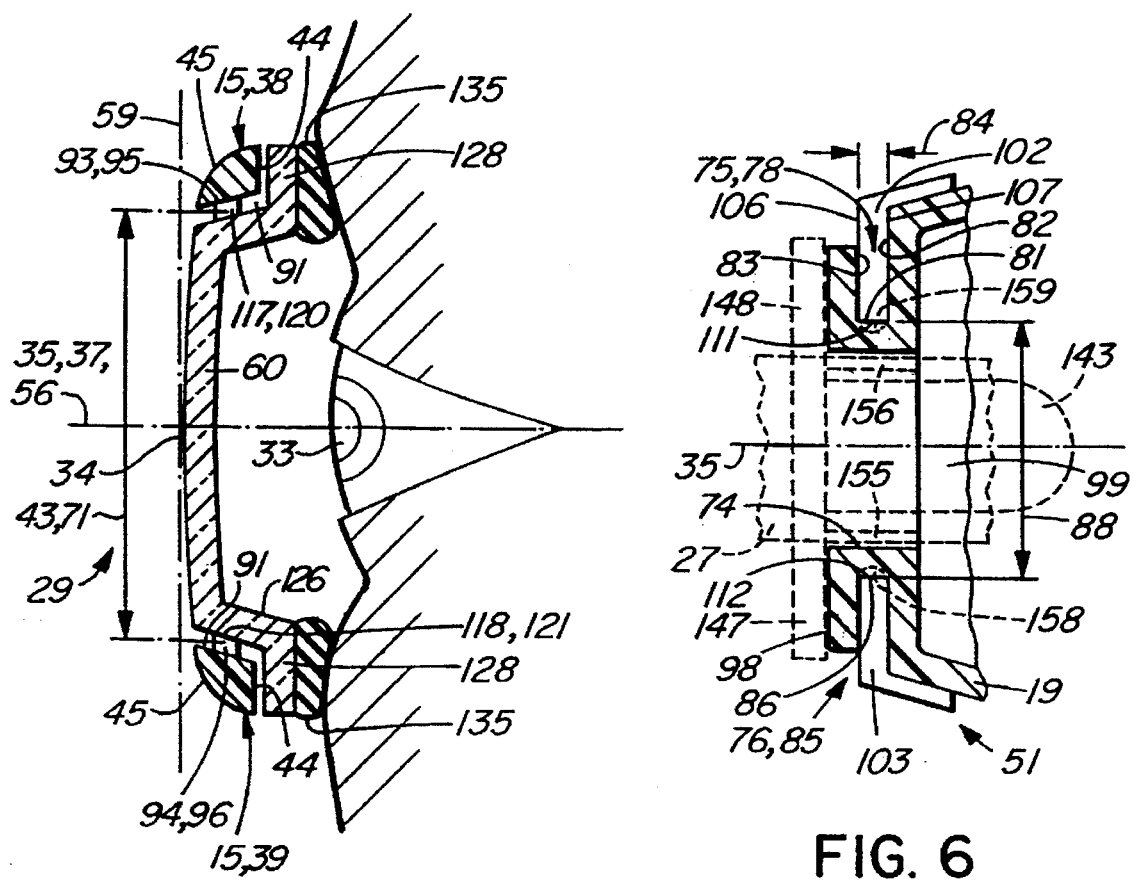
FIG. 5
FIG. 6

EYE GOGGLES WITH LATERALLY ADJUSTABLE EYEPIECES WITHIN GOGGLES FRAME

BACKGROUND OF THE INVENTION

The invention relates to eye goggles, in particular eye goggles as used for swimming.

Swimming goggles have been used for many years and, in general, comprise a pair of separate eyepieces interconnected at adjacent inner ends thereof by a nosepiece, and at oppositely located outer ends by a head strap adapted to pass around the head to secure the goggles to the face. Such goggles can be classified into two main types, namely goggles with essentially rigid nosepieces, and goggles with flexible nosepieces. Goggles with rigid nosepieces are usually more stable when fitted on the face, and thus do not easily become displaced and leak. Also, such goggles can be retained on the head with a relatively light head strap tension and they often more comfortable to wear than the other types of goggles. However, for some individuals, goggles with rigid nosepieces are awkward to fit as the nosepiece does not provide a wide range of adjustment of spacing between the eyepieces, which spacing is usually termed interocular separation or spacing. Thus, persons with eyes which are closer together or much wider apart than average can have difficulty in fitting goggles with rigid nosepieces which provide correctly spaced eyepieces with a secure and comfortable fit.

In contrast, goggles with flexible nosepieces are usually easy to adjust for a wide range of interocular spacing, but tend to be unstable when fitted on the face, and consequently require relatively high head strap tension to maintain a secure sealing fit. High head strap tension causes discomfort after a short while, and consequently such goggles are appropriate for short races, but tend to be uncomfortable for relatively long periods of wear.

There is also a third type of goggles comprising a one-piece goggles frame which has opposite ends interconnected by a head strap for securing to the head. The frame has a pair of eyepiece openings to receive respective eyepieces, the eyepieces being adjustable with respect to the eyepiece openings in the frame to accommodate spacing between the eyes of the person. An example of such goggles is found in U.S. Pat. No. 5,093,940 (Nishiyama). While this patent shows a means to easily adjust interocular spacing, the means of adjustment relies on friction to hold the eyepieces at the required interocular spacing. It has been found that the friction is sometimes insufficient to maintain the desired spacing of the eyepieces, causing the spacing between the eyepieces to inadvertently change, and thus such goggles often require frequent adjustment to maintain comfort and fit. In addition, the frame of Nishiyama is relatively flexible, and this also contributes to difficulty in adjusting the spacing of the eyepieces.

For persons requiring corrective lenses, that is refractive lenses, it is important that optical or ocular axes of the lenses coincide as closely as possible with the optical axes of the eyes. For such persons, accurate adjustment and maintenance of the interocular spacing of the eyepieces is important, as well as correct alignment of the eyepiece with respect to the eye. Consequently, when corrective lenses are used in goggles having a flexible nosepiece, difficulty can be experienced in positioning and maintained the eyepieces accurately with respect to the eyes to obtain adequate vision. Similarly, for goggles with essentially rigid nosepieces, adjustment of interocular spacing is also limited, and thus fitting corrective lenses to such goggles can be costly as spacing between the eyepieces must be individually adjusted to accommodate the person's eye spacing. For the third type of goggles exemplified by the above Nishiyama patent, while such structure permits easy adjustment of interocular spacing of the eyepieces, the spacing adjustment is easily lost and sometimes an eyepiece can rotate with respect to the frame, and thus frequent readjustment of the goggles would be necessary to attain satisfactory alignment of the optical axes.

SUMMARY OF THE INVENTION

The invention reduces the difficulties and disadvantages of the prior art by providing a pair of goggles in which spacing between the eyepieces is adjustable by moving the eyepieces with respect to an essentially rigid goggles frame with eyepiece openings containing the eyepieces. The goggles frame is characterized by an essentially rigid nosepiece which maintains eyepiece openings of the goggles frame at an essentially fixed distance, and the eyepieces are adjustable within each eyepiece opening and positively located therein to resist inadvertent movement which would otherwise tend to cause spacing between the eyepieces to change.

A pair of goggles according to the invention comprises a goggles frame, a pair of eyepiece units, and position adjusters. The goggles frame has a pair of eyepiece holders and a nosepiece extending between the eyepiece holders. Each eyepiece holder defines respective eyepiece openings therein having opposite inner and outer end portions spaced apart along an interocular axis to define length of the respective eyepiece opening. Each eyepiece holder has opposite side portions spaced apart transversely of the interocular axis to define width of the eyepiece opening. The eyepiece holders have inner end portions interconnected to the nosepiece and outer end portions connectable with a head strap. The eyepiece units are fitted within the respective eyepiece openings of the eyepiece holder and are spaced apart at an interocular spacing along the interocular axis. Each eyepiece unit has a lens and opposite inner and outer end portions spaced apart along the interocular axis to define length of the eyepiece unit which is smaller than length of the eyepiece opening. This permits relative movement between each eyepiece unit and the respective eyepiece holder along the interocular axis to permit adjustment of the interocular spacing. Each eyepiece unit has opposite side portions spaced apart transversely of the interocular axis to define width of the eyepiece unit which is approximately equal to the width of the respective eyepiece opening. The position adjusters permit adjustment of the position of each eyepiece unit within the respective eyepiece opening and include guides cooperating with the outer end portions and intermediate portions of the eyepiece units and the eyepiece openings. The guides guide axial movement of the eyepiece units along the interocular axis, and prevent rotation of each eyepiece unit relative to the respective eyepiece holder.

Preferably, the guides of the outer portions are characterised by the outer portion of each eyepiece holder having a holder track, and the outer portion of eyepiece unit having a respective eyepiece track. The eyepiece track is generally complementary to the holder track to permit sliding movement therealong. Preferably, the holder track and eyepiece track are disposed generally parallel to a plane containing the interocular axis to guide movement along the interocular axis. Preferably, the guides of the outer portions are characterised by two spaced apart holder tracks and eyepiece tracks as above defined. The position adjusters further include a locator cooperating with an eyepiece unit and the respective eyepiece holder to restrict the movement between the eyepiece unit and the eyepiece holder. Preferably, the locator is a spacer fitted between the eyepiece unit and the respective eyepiece holder to prevent relative movement therebetween.

A detailed disclosure following, related to drawings, describes a preferred embodiment of the invention which is capable of expression in structure other than that particularly described and illustrated.

BRIEF DESCRIPTION OF THE DRAWINGS

In drawings which illustrate a preferred embodiment of the invention,

FIG. 4 is a simplified perspective of an eyepiece unit for fitting within the eyepiece holder of FIG. 3, FIG. 5 is a simplified fragmented transverse cross section on Line 5—5 of FIG. 1 showing cooperation between intermediate guides of the eyepiece holder and the eyepiece unit, the goggles being shown located on a person's face, FIG. 6 is a simplified fragmented section on Line 6—6 of FIG. 2 showing cooperation between outer guides associated with outer portions of the eyepiece holder and the eyepiece unit, and also showing approximate position of a locator or spacer in broken outline as would be seen with structure of FIG. 10 using an extended spacer configuration, some portions not cross-hatched for clarity.

DETAILED DESCRIPTION

FIGS. 1 through 6

Figure 1:
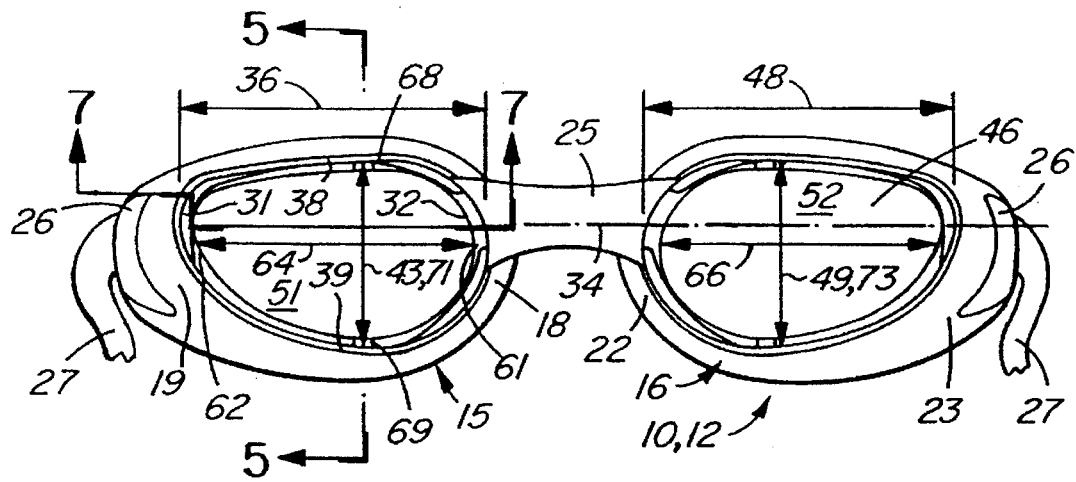
FIG. 1 is a simplified fragmented front elevation of a pair of goggles according to the invention, porions of a head strap of the goggles being shown fragmented.
Figure 2:
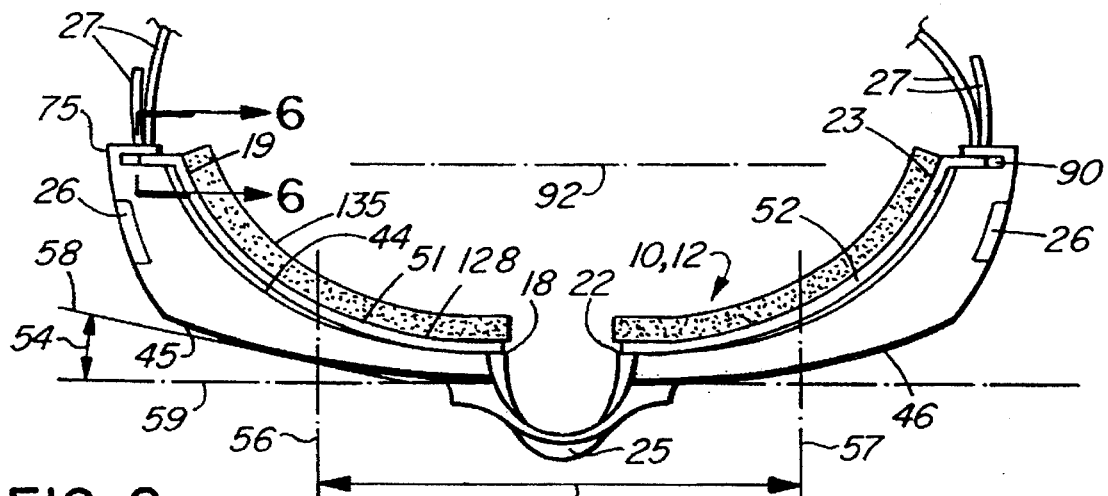
FIG. 2 is a simplified fragmented top plan view of the goggles of FIG. 1, showing some cooperating portions of the goggles.

Referring mainly to FIGS. 1 and 2, a pair of goggles 10 according to the invention comprise a relatively rigid goggles frame 12 having a pair of eyepiece holders, namely a first or right hand eyepiece holder 15, and a second or left hand eyepiece holder 16. The first eyepiece holder 15 has inner and outer end portions 18 and 19, and the second eyepiece holder 16 has inner and outer end portions 22 and 23 respectively. The goggles also comprise a nose piece 25 extending between and interconnecting the inner end portions 18 and 22 of the eyepiece holders, and an elastic head strap 27 extending between and interconnecting the outer end portions 19 and 23 of the holders 15 and 16 respectively. The head strap 27 is shown fragmented and clearly extends as a band to pass around the head to secure the goggles to the head as is well known. Conventional strap connectors and length adjustment means 26, not shown in detail, are incorporated in the outer end portions 19 and 23 of the holders, and permit connection and adjustment of the operative length of the head strap as is well known. The nose piece 25 is generally U-shaped as seen in FIG. 2 to bridge the nose of the person and is preferably sufficiently stiff and rigid to provide support between the relatively rigid eyepiece holders. The nosepiece and two eyepiece holders can be integral with each other for manufacturing simplicity, and can be made from a plastic material, e.g. polycarbonate which can be made to be sufficiently stiff to hold the eyepiece holders in an essentially fixed relationship relative to each other and to permit use of low head strap tension. Alternatively, the nosepiece can be rigidly connected to the eyepiece holders using a structure as disclosed in a co-pending U.S. patent application Ser. No. 07/866,984 of the present assignee. In this alternative, the nosepiece can be made from a different material, e.g. nylon which, in general, is considered to be tougher than polycarbonate.

Figure 3:
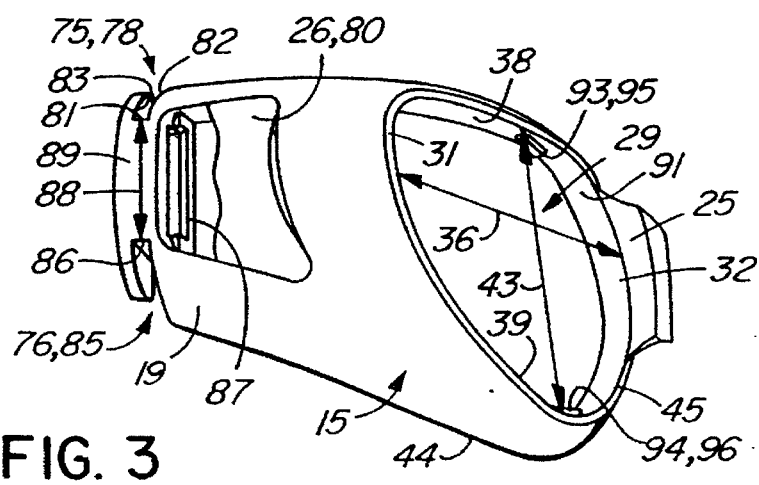
FIG. 3 is a simplified fragmented perspective of approximately one-half of a goggles frame, showing an eyepiece holder and a portion of a nosepiece.

As also seen in FIGS. 3 and 5, the first eyepiece holder 15 defines a first eyepiece opening 29 which has opposite inner and outer end portions 31 and 32 respectively which are spaced apart along an interocular axis 34 to define length 36 of the eyepiece opening. The interocular axis 34 is a reference datum which is selected for convenience to facilitate description of the goggles. Also, for convenience of reference, the terms "upper", "lower" and "horizontal", etc., as used herein refer to the goggles when worn on the person's face with the head in a normal vertical position, as shown in FIGS. 1 and 5. The interocular axis 34 is intersected by a horizontal plane 35, hereinafter "sight plane", which contains an optical axis 37 of a pupil 33 of a person's eye looking straight ahead, and is generally perpendicular to planes containing lenses of eyepieces to be described. For convenience of reference, the interocular axis 34 is defined as being within a sight plane which is coincident with or generally parallel to a usual line of sight, i.e. the optical axis 37 passing generally perpendicularly through the eyepiece.

The eyepiece holder 15 has opposite upper and lower side portions 38 and 39 respectively which are spaced transversely of the interocular axis 34 to define width 43 of the eyepiece opening 29. The eyepiece holder 15 has a rearward facing rear surface 44 curved to generally follow contours of the person's face, although, as seen in FIG. 5, this surface does not contact the face for reasons to be described. The eyepiece holder also has a forward facing front surface 45 which is generally flush with the lens as will be described.

The second eyepiece holder 16 has a second or left hand eyepiece opening 46, the opening and holder being an essentially mirror image of the opening 29 and holder 15 of the right hand side, with a similar length and width 48 and 49 extending between the appropriate portions of the eyepiece holder as previously described.

The goggles 10 further comprise a pair of eyepiece units, namely a first or right hand eyepiece unit 51 and a second or left hand eyepiece unit 52 which are received in the first and second eyepiece openings 29 and 46 respectively. The first and second eyepiece units are essentially mirror images of each other and are described in greater detail with reference to FIGS. 4 and 6. Optical data of the first and second eyepieces are defined with reference to first and second ocular axes 56 and 57 which are theoretically aligned with axes passing through the person's pupils, and clearly intersect the interocular axis 34. The eyepiece units are spaced apart at an interocular spacing 55, which is spacing along the axis 34 between the first and second ocular axes 56 and 57 of the eyepiece units 51 and 52 respectively.

As also seen in FIGS. 2, 4 and 5, the first eyepiece unit 51 has a first lens 60, the term "lens" being used to designate a thin transparent member which can be of constant thickness and essentially plane or slightly curved as shown, that is non-corrective, or it can have a variable thickness and be curved to provide corrective or refractive lenses for the person. The present invention is particularly useful for persons who need corrective lenses as the interocular spacing 55 can be accurately set and maintained to ensure that the interocular spacing of the lenses matches the spacing between optical axes of the person's eyes. Ignoring any curvature of the lens, the lens defines a lens plane 58 which is ideally perpendicular to the optical axis 37 or a usual line of sight passing through the eyepiece but in practice can be inclined at a shallow angle thereto. As seen in FIG. 5, a datum plane 59 is a theoretical plane disposed perpendicularly to the sight plane 35 and disposed generally tangentially and symmetrically to both eyepieces, and contains the interocular axis 34, see FIG. 2, and generally vertically when the person's head is upright. In FIG. 2, the lens plane 58 is shown disposed at an angle 54 to the datum plane 59, the angle being dependent on shape of the eyepiece holder and shape of the person's face. Clearly, a compromise might be necessary, and if the angle 54 is less than 15 degrees, any optical distortion is generally negligible.

The eyepiece unit 51 further comprises opposite inner and outer end portions 61 and 62 respectively which are spaced apart along the interocular axis to define length 64 of the eyepiece unit as measured at the lens 60. The length 64 is smaller than the length 36 of the eyepiece opening 29 to permit movement between the eyepiece unit 51 and the eyepiece holder 15. The second eyepiece unit 52 has a similar length 66 which is similarly smaller than the length 48 of the second eyepiece opening. Thus, the lengths of the eyepiece units are smaller than lengths of the respective eyepiece openings and thus the difference in length permits movement between each eyepiece unit and the respective eyepiece holder along the interocular axis 34 to adjust the interocular spacing 55.

In addition, the eyepiece unit 51 has upper and lower oppositely positioned side portions 68 and 69 which are spaced apart transversely of the interocular axis to define width 71 of the eyepiece unit. As will be described, the width 71 is approximately equal to the width 43 of the first eyepiece opening 29 and thus permits a snug but adjustable fit of the eyepiece unit within the eyepiece opening as seen in FIGS. 1 and 2. Similarly, the second eyepiece unit has a width 73 similarly approximately equal to the width 49 of the second eyepiece opening 46.

The above description discloses a pair of goggles having a goggles frame with a pair of eyepiece openings therein, and a pair of eyepiece units fitted within the respective eyepiece openings and spaced apart at an interocular spacing which can be varied along the interocular axis. The structure as described above is broadly functionally generally similar to that shown in the third type of goggles, which permits adjustment of interocular spacing between eyepieces located in a frame secured to the head, as exemplified by U.S. Pat. No. 5,093,940 (Nishiyama). In Nishiyama, lateral adjustment means are provided to locate the eyepieces with respect to the openings in the frames by use of two inwardly directed projections of the frame, which are received in slotted channels or recesses in the eyepieces. In Nishiyama the slotted channels of the eyepieces are moved with respect to the projections to vary interocular spacing, but Nishiyama relies on friction to restrict inadvertent movement of the eyepieces with respect to the frame. The friction between the eyepieces and the frame is often insufficient to prevent lateral and/or rotational relative movement between the frame or the eyepiece, and consequently the goggles frequently require re-adjustment. The present invention provides alternative means for adjusting location of the eyepiece units within the goggle frame and also provides a positive locking structure which has advantages over the structure of the Nishiyama patent.

FIGS. 2 through 7

In FIGS. 3 and 6, the outer end portion 19 of the eyepiece holder 15 has a pair of spaced apart holder tracks, namely an upper holder track 75, and a lower holder track 76 which serve as outer guide portions as will be described. The track 75 is a slot 78 extending inwardly from an outer upper surface of the holder, and has an end wall 81 and a pair of generally parallel oppositely facing flat side walls 82 and 83. The side walls 82 and 83 are parallel to each other and spaced apart from each other at a slot width 84 as best seen in FIG. 6. The lower holder track 76 is a slot 85 and is generally similar to and aligned vertically with the slot 78 of the track 75 and has an end wall 86 spaced from the end wall 81 by an end wall spacing 88. The end walls 81 and 86 are parallel to each other and are also generally parallel to the sight plane 35. Thus, the outer portion of the eyepiece holder has a pair of slots 78 and 85 extending inwardly from outer surfaces thereof to provide holder tracks 75 and 76, the slots having end walls 81 and 86 which are parallel to each other, and are also generally parallel to the sight plane 35 (FIG. 5) containing the interocular axes 34 and 56. As seen in FIG. 2, the track 75 or slot 78 is aligned with a corresponding track or slot 90 of the eyepiece holder 16 along a slot axis 92, which axis is generally parallel to the datum plane 59 for reasons to be described.

Figure 7:
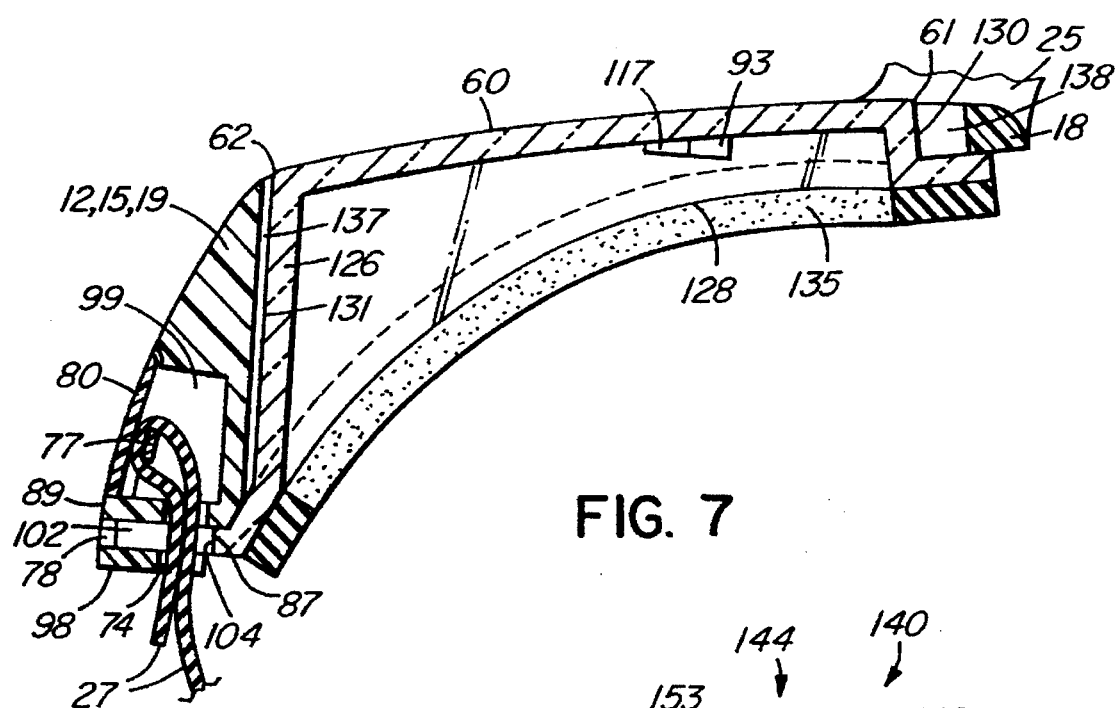
FIG. 7 is a simplified, fragmented longitudinal section on Line 7—7 of FIG. 1 with some cross-hatching eliminated for clarity, showing an eyepiece unit located in an outermost position with respect to the eyepiece holder, i.e. at a maximum interocular spacing setting, the Line 7—7 being staggered to illustrate outer guides as well as intermediate guides.

Inner portions of the end walls 81 and 86 are interconnected by an inwardly facing inner base wall 87 which is shown in broken outline in FIG. 3 and also is shown in end view in FIG. 7. Outer portions of the end walls 81 and 86 are interconnected by an outer base wall 89 facing outwardly from the eyepiece holder, the base wall portions being closely adjacent the connecting means 26 of the head strap 27 with the eyepiece holder 15. As seen in FIG. 7, the outer end portion 19 has a rectangular opening 74 passing through a rearwardly-facing rearmost surface 98 of the end portion 19, and through a space between the inner and outer base walls 87 and 89, and as seen in FIG. 6, between the end walls 81 and 86. The rectangular opening 74 passes into a cavity 99 within the end portion 19, the cavity 99 being normally closed by a detachable plate member 80 which fairs smoothly with an outer surface of the end portion 19 and has a bridge member 77 extending across an inner surface thereof. The head strap passes inwardly through the rectangular opening 74, around the bridge member 77 to form a loop, and returns outwardly through the rectangular opening 74 to a free end of the head strap. Thus, the connecting and length adjustment means 26 is fully enclosed within the outer end portion 19 and the strap passes unobtrusively through the outer guide means of the eyepiece.

As seen in FIGS. 3 and 5, the eyepiece holder 15 has an enclosed inner surface 91 defining the eyepiece opening 29 and supporting a pair of oppositely facing intermediate guide portions, namely upper and lower guide portions 93 and 94, extending inwardly towards each other as shown. The guide portions 93 and 94 are small elongated projecting platforms located on the side portions 38 and 39 of the holder and are generally parallel to each other and parallel to the interocular axis 34 or sight plane 35, as viewed in FIGS. 1 and 5. The guide portions 93 and 94 have inwardly facing oppositely disposed guide surfaces 95 and 96 which are generally flat and also parallel to each other, and also parallel to the sight plane 35, as best seen in FIG. 5.

Referring to FIGS. 4 and 6, the outer end portion 62 of the first eyepiece unit 51 has a pair of outwardly projecting flanges, namely upper and lower flanges 102 and 103 respectively which are interconnected by an eyepiece base wall 104. The upper flange 102 has a pair of generally parallel flange side walls 106 and 107 which are spaced apart at a flange thickness 109 which is slightly less than the slot width 84 of the slot 78 of the eyepiece holder so as to be received in the slot. The flange 102 has an inner wall 111 which is parallel to the sight plane 35 containing the interocular axis 34.

The flange 103 is generally similar to the flange 102 but is a mirror image thereof and has a similar inner wall 112 parallel to the wall 111. Thus, the flanges 102 and 103 have inwardly facing, oppositely disposed inner walls 111 and 112 which are parallel to each other and parallel to the sight plane 35 and serve as outer guide portions. The inner walls are spaced apart at an inner wall spacing 114 which is slightly greater than the end wall spacing 88 of the end walls 81 and 86 of the slots to provide outer guides for the eyepiece unit and eyepiece holder. Thus, the flanges 102 and 103 can pass into the respective slots 78 and 85 and the inner walls 111 and 112 of the flanges can engage the end walls 81 and 86 of the slots. Thus, the flanges 102 and 103 provide a pair of eyepiece tracks which are spaced apart at a spacing generally similar to spacing of the holder tracks and are generally complementary to the holder tracks to permit sliding movement therealong to vary position of the eyepiece unit within the eyepiece frame. Because the holder tracks and eyepiece tracks are disposed generally parallel to the sight plane 35 containing the interocular axis 34, the outer guides ensure that relative movement along the tracks changes interocular spacing.

As best seen in FIG. 4, the eyepiece unit 51 has a peripheral wall 126 extending around the lens 60 and having an undesignated outer edge flush with the lens as shown. The eyepiece unit has a pair of intermediate eyepiece guide members, namely upper and lower eyepiece guide members 117 and 118 respectively which are elongated projecting platforms extending from opposite sides of the wall 126 and located closely adjacent the lens. The guide members 117 and 118 have outwardly facing, oppositely disposed guide surfaces 120 and 121 which are generally flat and parallel to each other, and also parallel to the sight plane 35 containing the interocular axis.

As best seen in FIG. 5, the surfaces 120 and 121 of the eyepiece guide members 117 and 118 are engaged by the surfaces 95 and 96 respectively of the guide portions 93 and 94 of the eyepiece holders. For convenience, the widths 43 and 71 of the eyepiece opening 29 and the eyepiece unit 51 are shown extending between the guide surfaces 95 and 96 and 120 and 121 respectively, and are essentially equal as previously described. Preferably, there is a light interference fit between the guide surfaces which thus restricts movement of the eyepiece unit with respect to the eyepiece holder in a vertical plane. Also, in combination with the lateral restraint imposed by the slots 78 and 85 and complementary flanges 102 and 103 of the outer guides, the intermediate guide members also prevent any rotation of the eyepiece unit with respect to the eyepiece holder about the ocular axis 56, and also any relative rotation about the interocular axis 34.

Also, as best seen in FIGS. 4, 5, and 7, the wall 26 has an undesignated inner edge having a peripheral flange 128 extending therearound, the flange 128 extending outwardly from the peripheral wall on an edge of the wall remote from the lens 60. The peripheral wall 126 is of generally oval cross-section and the wall 126 and flange 128 are contoured to fit an average face. Thus, the wall 126 resembles a truncated oval cone or a hollow wedge so that when the flange 128 is adjacent the face, the lens is generally parallel or inclined at the shallow angle 54 to the datum plane 59, so as to be generally perpendicular to at least the usual line of sight passing therethrough. Thus, as best seen in FIG. 7, the peripheral wall 126 has an inner portion 130 which is adjacent the nose of the person and extends from the flange 128 a relatively short distance to the lens 60, and an outer portion 131 which is adjacent the temple or outer portion of the eye of the person and extends from the flange a much greater distance to the lens 60 to accommodate curvature of the face. A side of the flange 128 facing the face of the person is provided with a resilient gasket 135, suitably cut from an expanded synthetic rubber or plastic foam, to provide sealing contact with the person's face and to increase comfort.

As best seen in FIGS. 2 and 7, the wedge-like shape of the eyepiece unit 51 is generally complementary to the shape of the eyepiece holder 15. The gasket 135 projects inwardly towards the person's face from a rear surface of the flange 128 of the eyepiece unit and, as best seen in FIG. 5, both the eyepiece unit 51 and the eyepiece holder 15 are prevented from contacting the person's face by the resilient gasket 135.

In the structure above, the eyepiece units are relatively free to move within the eyepiece holders, so as to vary the interocular spacing between a minimum spacing in which the eyepiece units are closest to the respective inner end portions (e.g. 31) of the respective eyepiece openings, to a maximum interocular spacing, in which the eyepiece units are closest to the respective outer end portions (e.g. 32) of the respective eyepiece openings. It has been found that inclined surface of the flange 128 surrounding the wedge-like shape of the eyepiece units produces an outwardly directed force between the eyepiece unit and the respective eyepiece holder when the goggles are worn on an average face. Without a positive restraint, this outwardly directed force causes the eyepiece units to gradually move outwardly with respect to the eyepiece holders to tend to attain the widest interocular spacing, which is as seen in FIG. 7 and is appropriate only for those persons with widely set apart eyes.

Referring to FIG. 7, in the widest interocular spacing an inwardly located portion of the upper guide member 117 of the eyepiece unit 51 engages an outwardly located portion of the upper guide portion 93 of the eyepiece holder 15 and the flange 102 of the eyepiece unit is shown fully received in the slot 78 of the eyepiece holder. In the widest interocular spacing as shown, the eyepiece base wall 104 is shown held against the inner base wall 87 of the eyepiece holder, which thus prevents further outwards movement of the eyepiece unit with respect to the eyepiece holder. In this relative position, an outer space 137 between the outer end portion 62 of the eyepiece, and an inner surface of the outer end portion 19 of the eyepiece holder is relatively narrow with respect to the interocular axis, whereas an inner space 138 between the inner and end portions 61 and 18 is relatively wide. Clearly the guide members and guide portions have adequate lengths to maintain engagement with each other to accommodate total eyepiece unit movement between minimum and maximum interocular spacing. Similarly, the flanges 102 and 103 and the slots 78 and 85 have sufficient length to accommodate the total movement of the eyepiece with respect to the eyepiece holder.

For most other persons having eyes set closer together, locator means are required to locate the eyepieces in a fixed intermediate position where the interocular spacing is less than maximum. This is attained by providing a locator which cooperates with a particular eyepiece unit and its respective eyepiece holder to restrict inadvertent movement between the eyepiece unit and the eyepiece holder. One example of a locator with a variable thickness is to be described with reference to FIGS. 8 through 11, although many alternatives are envisaged to serve a similar purpose.

FIGS. 8 through 11

Figure 8:
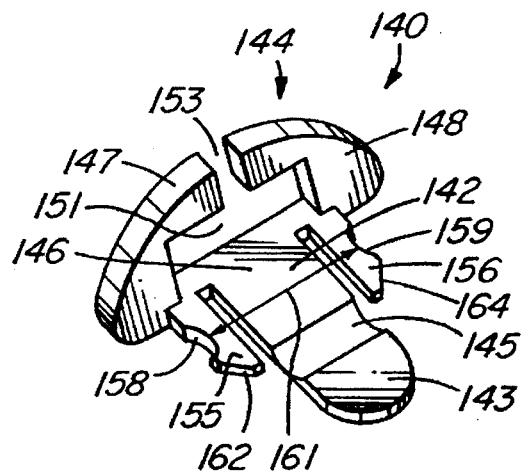
FIG. 8 is a perspective of a spacer according to the invention, the spacer being shown extended or unfolded.
Figure 9:
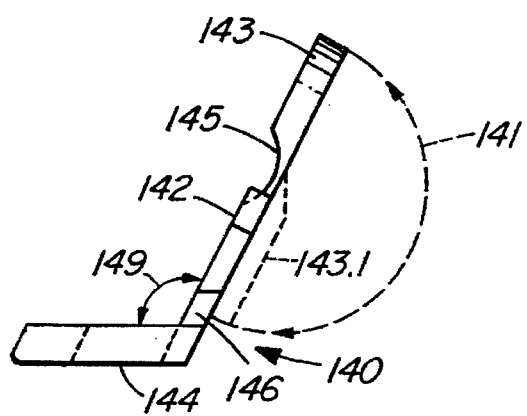
FIG. 9 is a simplified end elevation of the spacer of FIG. 8, the spacer also being shown folded in broken outline.

Referring to FIGS. 8 and 9, one example of a locator is a spacer 140 which has inner and outer spacer portions 142 and 143 which are interconnected by a hinge portion 145, which is preferably a film hinge which permits hinging movement per broken outline arrow 141 between the portions 142 and 143 for reasons to be described. The hinge portion permits the spacer to be folded so that the outer portion, shown in broken outline at 143.1, lies against the inner portion 142 to decease overall thickness of the spacer to vary spacing between the eyepiece unit and the eyepiece holder as will be described.

The spacer 140 also includes a strap retainer 144 which extends obliquely from a base portion 146 of the spacer.

The strap retainer comprises first and second strap retainer portions 147 and 148 which are mirror images of each other and coplanar with each other. The portion 147 and 148 extend at an oblique angle 149 to the inner spacer portion 142 to define a strap receiving opening 151 therebetween which receives two portions of the head strap 27 passed therethrough as will be described. The strap retaining portions 147 and 148 have outer ends spaced apart to define a narrow gap 153 therebetween which communicates with the opening 151 and facilitates threading of the strap. Thus the spacer has the opening 151 therein to receive the head strap to pass therethrough to assist in retaining the spacer with the goggles, which not only serves to prevent loss of the spacer as will be described, but also provides an unobtrusive means of retaining the spacer with the goggles.

The spacer 140 also has first and second tangs 155 and 156 which extend parallel to edges of the inner portion 142 and are coplanar with the inner portion. The tangs 155 and 156 are spaced from the edges of the inner portion and are sufficiently flexible to be deflected towards the inner portion as required. Outer edges of the tangs 155 and 156 are provided with arcuate recesses 158 and 159 which have innermost portions separated by spacing 161 which is approximately equal to the spacing 114 between the flanges 102 and 103 of the outer portion of the eyepiece 61, see FIG. 4. Outer portions 162 and 164 of the tangs 155 and 156 are tapered to facilitate insertion of the spacer between the flanges adjacent the outer end portion 62 as will be described.

Figure 10:
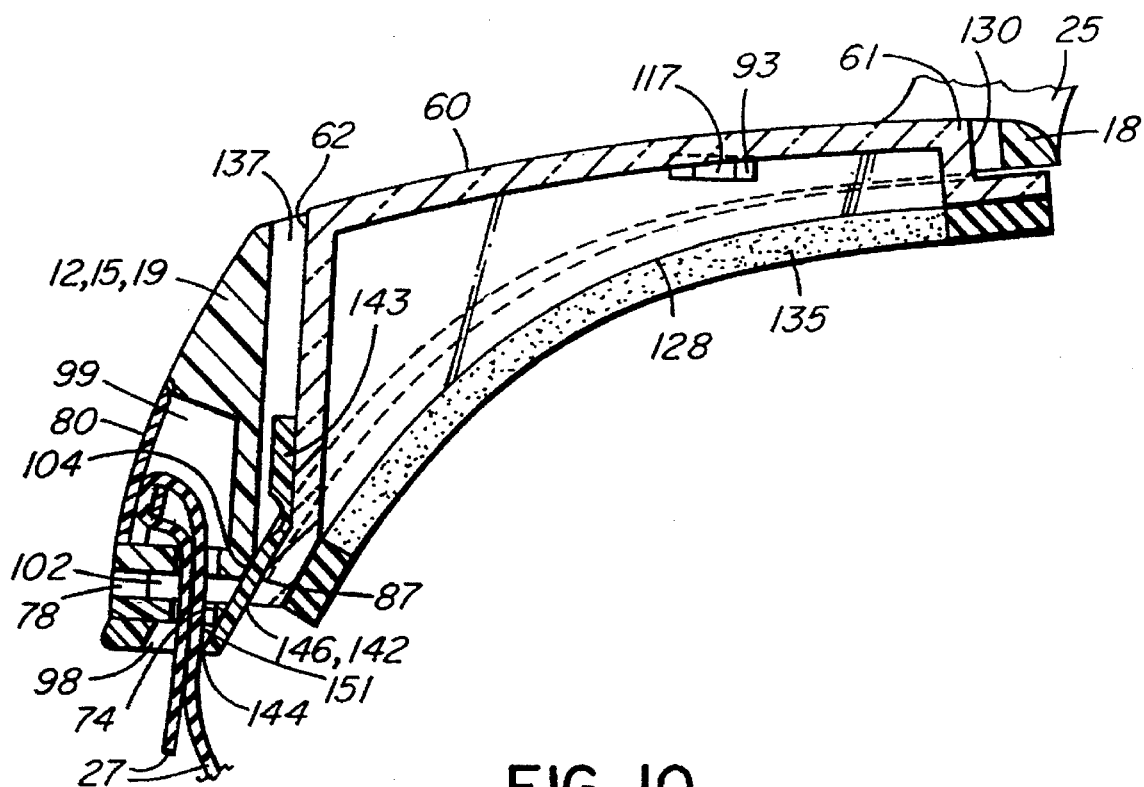
FIG. 10 is a simplified, fragmented longitudinal section generally similar to FIG. 7 but showing the eyepiece in an intermediate position with respect to an eyepiece holder, i.e. at an intermediate interocular spacing, the spacer of FIG. 8 being shown cross-hatched, extended and inserted between the eyepiece holder and the eyepiece unit.

In FIG. 10, the eyepiece unit 61 is shown in an intermediate position with respect to the eyepiece holder 15, and the spacer 140 is shown extended, i.e. unfolded or in a minimum thickness position interposed between the outer end portion 62 of the eyepiece unit 51 and the adjacent outer end portion 19 of the eyepiece holder. In this position, the base portion 146 of the inner spacer portion 142 is sandwiched between the inner base wall 87 of the eyepiece holder 15, and the eyepiece base wall 104 of the eyepiece unit 51. Thus, it can be seen that the spacer is fitted between the eyepiece unit and respective eyepiece holder to prevent relative movement therebetween. The strap retainer 144 of the spacer is held flush against the rearmost surface 98 of the end portion 19 and the opening 151 of the retainer 144 is aligned with the opening 74 through which two portions of the strap 27 protrude.

In FIG. 6, the spacer is shown in broken outline as fitted in FIG. 10, and the recesses 158 and 159 of the tangs 155 and 156 respectively are received between the inner walls 112 and 111 of the flanges 103 and 102 respectively of the eyepiece unit. Interference between the tangs and the flanges prevents movement of the spacer 140 away from the surface 98, even when the goggles are removed from the face. In addition, residual tension in the strap portions can apply an inwards force holding the strap retainer 144 against the surface 98. Clearly, only while the goggles are retained on the face is there an outwardly directed force tending the hold the eyepiece units against the outer end portions of the eyepiece holders. The spacer 140 prevents outward movement of the eyepiece unit relative to the respective eyepiece openings that would otherwise occur due to the angle of the eyepiece unit resting on the face.

In FIG. 10, it is seen that the base portion 146 and the inner portion 142 of the spacer are sandwiched between the outer end portion 19 of the eyepiece holder 15, and the outer end portion of the eyepiece unit 51. The outer spacer portion 143 is located in the outer space 137 between the outer end portion 19, and the outer portion 62 of the eyepiece unit 51. In this position there is sufficient space between the two outer portions to receive the outer spacer portion 143 without interference therewith and thus the outer portion of the spacer is not trapped and therefor does not function as a spacer. Size of the space 137 in FIG. 10 contrasts with size of the space 137 in FIG. 7, where the end portion 62 is close to the end portion 19. Interference between the flanges 102 and 103 of the eyepiece units and the slots 78 and 85 of the holder 15 and the recesses 158 and 159 respectively of the spacer assist in restricting inadvertent movement of the eyepiece unit with respect to the eyepiece holder, thus ensuring interocular spacing remains unchanged, whether the goggles are worn or removed.

Figure 11:
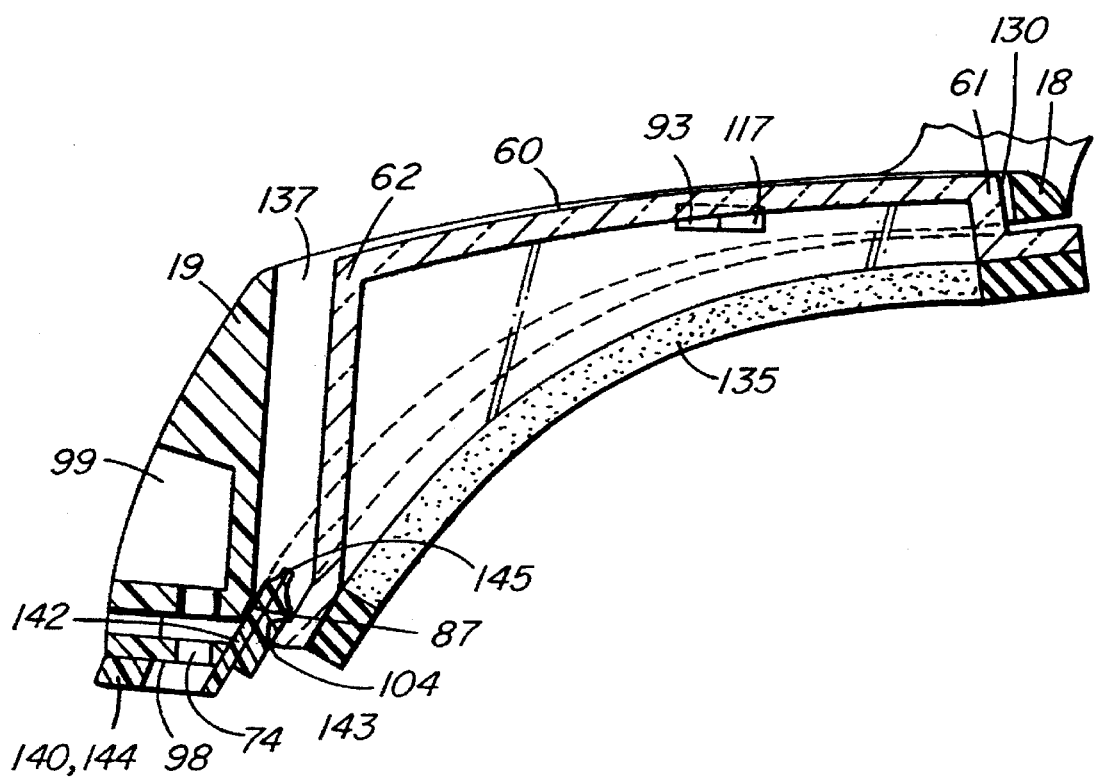
FIG. 11 is a simplified, fragmented longitudinal section generally similar to FIG. 10 but showing the eyepiece unit in an innermost position with respect to the eyepiece holder, i.e. at a minimum interocular spacing position, with the spacer being shown cross-hatched, folded and inserted between the eyepiece holder and the eyepiece unit, and the head strap and other portions being omitted for clarity.

Referring to FIG. 11, the eyepiece unit 51 is located at an innermost position with respect to the eyepiece holder 15, and thus the outer space 137 between the eyepiece unit and outer end portion 19 is at a maximum, and the inner space 138 between the eyepiece unit and the inner end portion 18 is at a minimum. In this position, an outwardly located portion of the upper intermediate guide member 117 of the eyepiece unit 51 engages an inwardly located porion of the upper guide portion 93 of the eyepiece holder 15.

This innermost setting of the eyepiece is attained by folding the spacer 140 about the hinge portion 145, (see FIG. 9) so that the inner spacer portion 142 contacts and lies against the outer portion 143. The inner spacer portion 142 contacts the inner base wall 87 as in FIG. 10, whereas the outer spacer portion 143, folded against the portion 142, contacts the eyepiece base wall 104. Thus, in this position, interference between the inner base wall 87, the folded spacer and the outer portion of the eyepiece holder prevents the eyepiece unit from moving further outwardly. Thus, it can be seen that the spacer has a variable thickness, i.e. a single thickness or double thickness, to vary spacing between the eyepiece unit and the respective eyepiece holder.

Because the nosepiece is relatively stiff, the present goggles can be worn with relatively light head strap tension. Operative length of the head strap is adjusted using the means 26 so that the goggles fit snugly on the face, with the resilient sealing gasket 135 being lightly compressed against the face. Spacing between the eyepiece units is adjusted so that optical axes of the eyes can be aligned quite accurately with the ocular axes of the eyepiece units. For a relatively symmetrical normal face, the spacers 140 are used in one of the two positions as shown in FIG. 10 or 11, or if the person has relatively widely spaced eyes, the spacers can be eliminated altogether and the eyepiece units are set to the widest spacing as shown in FIG. 7.

For persons with asymmetrical faces, it is possible to use the spacers in different configurations for each side of the goggles, for example a single thickness of a first spacer could be used on one side to position the respective eyepiece unit in an intermediate position as shown in FIG. 10, and the second spacer could be folded to assume a double thickness configuration on the opposite side, as shown in FIG. 11. It can be seen that the goggles can be used with a total of six configurations of the spacer, each eyepiece/holder having three different configurations as follows: (i) no spacer; (ii) single thickness spacer; and (iii) double thickness spacer. For spacer portions 142 and 143 each having a nominal thickness of 1 millimeter, this provides a range of discrete or incremental adjustment of interocular spacings of between 0 and 5 millimeters in 1 millimeter increments, as there is a total of five different spaces.

It can be seen that the present invention provides position adjusters to permit adjustment of the position of each eyepiece unit within the respective eyepiece opening. The position adjusters include the slots 78 and 85 and the complementary flanges 102 and 103 which serve as outer end guides cooperating with outer end portions of the eyepiece units and the eyepiece openings. Similarly, the upper and lower guide portions 93 and 94 of the eyepiece holder 15, and the upper and lower guide members 117 and 118 of the eyepiece unit 51 serve as intermediate guides cooperating with intermediate or adjacent side portions of the eyepiece units and the eyepiece openings. The guides are spaced apart at three locations and thus provide a stable structure which provides guiding axial movement of the eyepiece units along the interocular axis, and simultaneously prevent rotation of each eyepiece unit relative to the respective eyepiece holder either about the ocular axis of the lens or about the interocular axis 34. By spacing the three guide portions widely apart, stability of the eyepiece unit within the eyepiece is attained, reducing any tendency for inadvertent movement therebetween.

The nosepiece is selected to be made of a material that is sufficiently stiff to hold a position, but can be bent, at room temperature, to a slightly different position, and will retain that position. This permits further finer, non-incremental adjustment of between approximately 1 or 2 millimeters, which provides an overall, non-incremental or stepless range of adjustment of about 7 millimeters which would accommodate eye spacings of about 95–97 per cent of persons of a typical population.

It can be seen that the spacer 140 resists the outwardly directed forces between the eyepiece unit and respective eyepiece holder when the goggles are worn, and thus force from the goggles tends to locate the spacer in the pre-set position. When the goggles are removed from the face, there is no outwards force generated on the eyepiece unit with respect to the eyepiece frame. However, because the width 43 of the eyepiece opening between the guide surfaces 95 and 96 is slightly less than the width 71 of the eyepiece unit between the guide surfaces 120 and 121, there is an intermediate located gripping force between the eyepiece unit and the eyepiece holder which tends to resist any inadvertent movement of the eyepieces. In addition, there is sufficient friction between the slots 78 and 85, and the flanges 102 and 103, which, in combination with force between the flanges and the spacer tends to resist any inadvertent movement of the eyepiece with respect to the holder. Consequently, when the goggles are removed from the face, there is little tendency for the interocular spacing to come out of adjustment.

For persons with corrective or refractive lenses, it is important that the interocular spacing or relative angular relationship between the lenses does not change inadvertently, and thus if necessary small amounts of adhesive can be applied to the guide surfaces 95, 96, 120 and 121 to essentially bond the eyepiece unit with respect to its eyepiece holder. If necessary, the bonding can be augmented by placing additional adhesive between the flanges and the slots. Clearly, once this has been done, the goggles are no longer adjustable to suit other persons, but this would not be a problem as usually goggles fitted with corrective lenses are not interchangeable between different persons.

ALTERNATIVES

The outer guides are shown to be a pair of flanges 102 and 103 of the eyepiece, which engage complementary slots 78 and 85 of an eyepiece holder to ensure movement of the eyepiece with respect to the eyepiece holder along the interocular axis. In the embodiment as shown, the guides of the outer portions have a pair of spaced apart holder tracks, and a pair of spaced apart eyepiece tracks. Clearly, in an alternative a single holder track could be substituted, which would be engaged by a single eyepiece track to attain similar guiding movement between the eyepiece holder and the eyepiece unit. Similarly, the intermediate guides, namely the inwardly and outwardly projecting platforms of the eyepiece holder and the eyepiece unit could be changed to suit particular requirements. Clearly, at least one portion of both types of guides have a guide surface which is generally parallel to a plane containing the two interocular axes.

In the present invention, the spacer 140 resembles a shim which is interposed between the outer portion of each eyepiece unit and the adjacent outer portion of each eyepiece opening to prevent outward movement of the eyepiece unit relative to the respective eyepiece opening. The spacer has a variable thickness to vary spacing between the unit and the holder to provide different interocular spacings. Clearly, alternative means of providing a positive restriction against movement of the eyepiece unit along the eyepiece holder can be substituted for the spacer, for example a dowel could be fitted in aligned openings provided in the eyepiece unit and the eyepiece holder to provide positive location against inadvertent movement between the eyepiece unit and eyepiece holder. The eyepiece unit and eyepiece holder could each have a plurality openings to permit a relatively fine incremental variation in interocular spacing, depending on which openings were aligned to receive the dowel therethrough.

We claim:

1. A pair of goggles comprising:

(a) a goggles frame having a pair of eyepiece holders and a nosepiece extending between the eyepiece holders, each eyepiece holder defining respective eyepiece openings therein having opposite inner and outer end portions spaced apart along an interocular axis to define a length of the respective eyepiece opening, each eyepiece holder having opposite side portions spaced apart transversely of the interocular axis to define a width of the eyepiece opening, the eyepiece holders having inner end portions interconnected to the nosepiece and outer end portions connectable with a head strap, (b) a pair of eyepiece units fitted within the respective eyepiece openings of the eyepiece holder, each eyepiece unit having a lens with a respective ocular axis, the ocular axes of the lenses being spaced apart at an interocular spacing along the interocular axis, each eyepiece unit having opposite inner and outer end portions spaced apart along the interocular axis to define a length of the eyepiece unit which is smaller than the length of the eyepiece opening to permit relative movement between each eyepiece unit and the respective eyepiece holder along the interocular axis to permit adjustment of the interocular spacing, each eyepiece unit having opposite side portions spaced apart transversely of the interocular axis to define a width of the eyepiece unit which is approximately equal to the width of the respective eyepiece opening, and (c) position adjusters to permit adjustment of the position of each eyepiece unit within the respective eyepiece opening, each position adjuster comprising end and intermediate guides provided adjacent at least one end portion and one side portion of each respective eyepiece unit and associated eyepiece holder so as to be spaced apart at three locations for each eyepiece unit and associated eyepiece holder to provide stability for guiding axial movement of the eyepiece units along the interocular axis, and for preventing rotation of each eyepiece unit relative to the respective eyepiece holder.

2. A pair of goggles as claimed in claim 1, in which the guides are characterized by:
(a) each guide having at least one guide surface which is generally parallel to a plane containing the ocular axes of the lenses of the eyepiece units.

3. A pair of goggles as claimed in claim 1, in which:
(a) the end guide is an outer end guide located adjacent the outer end portions of each eyepiece unit and associated eyepiece holder.

4. A pair of goggles as claimed in claim 1, in which:
(a) each intermediate guide is provided on oppositely located side portions of the eyepiece unit and associated eyepiece holder.

5. A pair of goggles as claimed in claim 3 in which the guides of the outer end portions are characterized by:
(a) the outer end portion of each eyepiece holder having a holder track, and
(b) the outer end portion of each eyepiece unit having a respective eyepiece track, the eyepiece track being generally complementary to the holder track to permit sliding movement therealong.

6. A pair of goggles as claimed in claim 5 in which:
(a) the holder track is disposed generally parallel to a plane containing the interocular axis, and
(b) the eyepiece track is disposed generally parallel to a plane containing the interocular axis.

7. A pair of goggles as claimed in claim 6 in which:
(a) the plane containing the interocular axis is a sight plane which is generally parallel to a usual line of sight passing through the eyepiece unit.

8. A pair of goggles as claimed in claim 6 in which:
(a) the plane containing the interocular axis is a lens plane which is generally perpendicular to a usual line of sight passing through the eyepiece unit.

9. A pair of goggles as claimed in claim 3 in which the guides of the outer end portions are characterized by:
(a) the outer end portion of each eyepiece holder having a pair of spaced apart holder tracks,
(b) the outer end portion of each eyepiece unit having a pair of respective eyepiece tracks, the eyepiece tracks being spaced apart at a spacing generally similar to spacing of the holder tracks and being generally complementary to the holder tracks to permit sliding movement therealong.

10. A pair of goggles as claimed in claim 9 in which:
(a) the holder tracks are disposed generally parallel to a plane containing the interocular axis, and
(b) the eyepiece tracks are disposed generally parallel to a plane containing the interocular axis.

11. A pair of goggles as claimed in claim 9 in which:
(a) the plane containing the interocular axis is a sight plane which is generally parallel to a usual line of sight passing through the eyepiece unit.

12. A pair of goggles as claimed in claim 9 in which:
(a) the plane containing the interocular axis is a lens plane which is generally perpendicular to a usual line of sight passing through the eyepiece unit.

13. A pair of goggles as claimed in claim 9 in which:
(a) the outer end portion of each eyepiece holder has a pair of slots extending inwardly from outer surfaces thereof to provide the respective holder tracks, the slots having end walls which are parallel to each other and parallel to a plane containing the interocular axis, each slot having a pair of side walls extending outwardly from the respective end wall and disposed parallel to each other, space between the side walls of each slot defining width of the slot, and
(b) the outer end portion of each eyepiece unit has a pair of outwardly projecting flanges to provide the respective eyepiece tracks, the flanges having inwardly facing, oppositely disposed inner walls which are parallel to each other and parallel to a plane containing the interocular axis, each flange having a pair of generally parallel flange side walls spaced apart at a thickness slightly less that the width of a respective slot of the eyepiece holder to be received in the respective slot, so that the flanges can pass into the respective slots and the inner walls of flanges can engage the end walls of the slots.

14. A pair of goggles as claimed in claim 13 in which:
(a) the end walls of the slots and the inner walls of the flanges are disposed parallel to a sight plane which is generally parallel to a usual line of sight passing through the eyepiece unit.

15. A pair of goggles as claimed in claim 13 in which:
(a) the slots and flanges are disposed generally parallel to a lens plane which is generally perpendicular to a usual line of sight passing through the eyepiece unit.

16. A pair of goggles as claimed in claim 1 in which the position adjusters further include:
(a) a locator cooperating with an eyepiece unit and a respective eyepiece holder to restrict movement between the eyepiece unit and the eyepiece holder.

17. A pair of goggles as claimed in claim 16 in which:
(a) the locator is a spacer fitted between the eyepiece unit and the respective eyepiece holder to prevent relative movement therebetween.

18. A pair of goggles as claimed in claim 17 in which:

(a) the spacer is interposed between the outer portion of each eyepiece unit and the adjacent outer portion of each eyepiece opening to prevent outward movement of the eyepiece unit relative to the respective eyepiece opening.

19. A pair of goggles as claimed in claim 18 in which:

(a) the spacer has a variable thickness to vary spacing between the eyepiece unit and the respective eyepiece holder.

20. A pair of goggles as claimed in claim 19 in which:

(a) the spacer has inner and outer spacer portions which are interconnected by a hinge portion, the hinge portion permitting the spacer to be folded so that the inner and outer spacer portions lie against each other to increase overall thickness of the spacer.

21. A pair of goggles as claimed in claim 17 in which:

(a) the spacer has an opening therein to receive the head strap to pass therethrough to retain the spacer with the goggles.

22. A pair of goggles as claimed in claim 4 in which the guides of the intermediate portions are characterized by:

(a) the eyepiece opening of each eyepiece holder having a pair of oppositely facing guide portions, the guide portions being located on the side portions of each holder and being generally parallel to each other and to the interocular axis, and (b) each eyepiece unit having a pair of eyepiece guide members on opposite side portions thereof, the eyepiece guide members being disposed within planes generally parallel to the interocular axis and spaced apart at a spacing within a range from generally equal to or slightly less than spacing between the guide portions of the eyepiece holders.

23. A pair of goggles as claimed in claim 22 in which:

(a) the guide portions of the eyepiece holders have inwardly facing, oppositely disposed guide surfaces which are generally flat and parallel to each other, and (b) the guide members of each eyepiece unit have outwardly facing, oppositely disposed guide surfaces which are generally flat and parallel to each other.

* * * * *